US006657070B2

(12) United States Patent
Resnick

(10) Patent No.: US 6,657,070 B2
(45) Date of Patent: Dec. 2, 2003

(54) PRODUCTION OF CHIRALLY PURE α-AMINO ACIDS AND N-SULFONYL α-AMINO ACIDS

(75) Inventor: Lynn Resnick, Edison, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/166,896

(22) Filed: Jun. 11, 2002

(65) Prior Publication Data

US 2003/0013892 A1 Jan. 16, 2003

Related U.S. Application Data

(63) Continuation-in-part of application No. 10/014,304, filed on Dec. 11, 2001.
(60) Provisional application No. 60/255,105, filed on Dec. 13, 2000.

(51) Int. Cl.$^7$ ............................................. C07D 333/32
(52) U.S. Cl. ......................................................... 549/65
(58) Field of Search .......................................... 549/65

(56) References Cited

U.S. PATENT DOCUMENTS

| 5,464,853 A | 11/1995 | Chan et al. |
| 5,514,691 A | 5/1996 | Chan et al. |
| 5,571,821 A | 11/1996 | Chan et al. |
| 5,591,761 A | 1/1997 | Chan et al. |
| 5,593,846 A | 1/1997 | Schenk |
| 5,594,021 A | 1/1997 | Chan et al. |
| 5,624,937 A | 4/1997 | Reel |
| 5,703,129 A | 12/1997 | Felsenstein |
| 5,852,007 A | 12/1998 | Chatterjee |
| 5,981,168 A | 11/1999 | Reiner |
| 6,248,775 B1 * | 6/2001 | Vazquez et al. ............ 514/445 |
| 6,376,523 B1 | 4/2002 | Chan et al. |
| 6,566,536 B2 * | 5/2003 | Muller et al. ................. 549/65 |
| 2002/0183361 A1 | 12/2002 | Kreft et al. |

FOREIGN PATENT DOCUMENTS

| EP | 510700 A2 | 10/1992 |
| EP | 652009 A1 | 5/1995 |
| EP | 1088821 A1 | 4/2001 |
| EP | 1172361 A1 | 1/2002 |
| JP | 5-148233 U | 6/1993 |
| JP | 11-343279 U | 12/1999 |
| WO | WO95/29904 A1 | 11/1995 |
| WO | WO98/03166 A1 | 1/1998 |
| WO | WO98/22104 A3 | 5/1998 |
| WO | WO98/22493 A2 | 5/1998 |
| WO | WO00/09107 A2 | 2/2000 |
| WO | WO00/50391 A1 | 8/2000 |
| WO | WO00/27108 A1 | 4/2001 |
| WO | WO01/23379 A1 | 4/2001 |
| WO | WO01/27091 A1 | 4/2001 |

OTHER PUBLICATIONS

A. Larner et al, "Review—Central & Peripheral Nervous Systems—Alzheimer's Disease: Towards Therapeutic Manipulation of the Amyloid Precursor Protein and Amyloid β–peptides", Exp. Opin. Ther. Patents, 7(10):1115–1127 (1997).
C. Moore et al, "Inhibition of β–amyloid Formation as a Therapeutic Strategy", Exp. Opin. Ther. Patents, 9(2):135–146 (1999).
V. John et al, "Alzheimer's Disease: Recent Advances on the Amyloid Hypothesis", in Annual Reports in Medicinal Chemistry, Chapter 2, pp. 11–20 (1997).
G. Rishton et al, "Fenchylamine Sulfonamide Inhibitors of Amyloid β Peptide Production by the γ–Secretase Proteolytic Pathway: Potential Small–Molecule Therapeutic Agents for the Treatment of Alzheimer's Disease", J. Med. Chem., 43(12):2297–2299 (Jun. 15, 2000).
B. Testa et al, "Prodrugs Revisited: The "Ad Hoc" Approach as a Complement to Ligand Design", Medicinal Research Reviews, 16(3):233–241 (May, 1996).
D. Skovronsky et al, "β–Secretase Revealed: Starting Gate for Race to Novel Therapies for Alzheimer's Disease", TIPS, 21:161–163 (May, 2000).
A. Ghosh et al, "Design of Potent Inhibitors for Human Brain Memapsin 2 (β–Secretase)", J. Am. Chem. Soc., 122:3522–3523 (2000).
W. Esler et al, "Transition–State Analogue Inhibitors of γ–Secretase Bind Directly to Presenilin–1", Nature Cell Biology, 2:428–434 (Jul. 2000).
Y–M. Li et al, "Photoactivated γ–Secretase Inhibitors Directed to the Active Site Covalently Label Presenilin 1", Nature, 405:689–694 (Jun., 2000).
M. Wolfe et al, "A Substrate–Based Difluoro Ketone Selectively Inhibits Alzheimer's γ–Secretase Activity", J. Med. Chem., 41:6–9 (Jan. 1, 1998).
S. Sinha et al, "Purification and Cloning of Amyloid Precursor Protein β–Secretase from Human Brain", Nature, 402:537–540 (Dec., 1999).

(List continued on next page.)

Primary Examiner—Deborah C. Lambkin
(74) Attorney, Agent, or Firm—Howson and Howson

(57) ABSTRACT

Methods for production of chirally pure α-amino acids and N-sulfonyl α-amino acids are described. An aldehyde and a cyanide salt are reacted with an α-methylbenzylamine to afford product. The product reacts with a strong acid, neutralized, and extracted. The resulting product is hydrolyzed to provide a product which is dissolved in a strong acid to provide a salt of a chirally pure α-amino acid, which is reacted to provide the chirally pure α-amino acid. Another method involves mixing ephedrine hemihydrate and an N-sulfonyl α-ethylnorvaline in ethanol at a molar ratio of 1:1; heating the mixture to dissolve the solids; cooling to allow formation of a precipitate; washing with an organic solvent to give diastereomeric salt; recrystallizing the salt; dissolving the recrystallized salt in an organic solvent and strong aqueous acid, separating the layers; washing the organic extract; drying and concentrating to provide chirally pure N-sulfonyl α-amino acid.

38 Claims, No Drawings

OTHER PUBLICATIONS

A. Goate, "Monogenetic Determinants of Alzheimer's Disease: APP Mutations", CMLS Cell. Mol. Life Sci., 54:897–901 (Sep., 1998).

M. Sabbagh et al, "β–Amyloid and Treatment Opportunities for Alzheimer's Disease", Alzheimer's Disease Review, 3:1–19 (1997).

C. Augelli–Szafran et al, β–Amyloid as a Target for Alzheimer's Disease Therapy, in Annual Reports in Medicinal Chemistry, Chapter 3, pp. 21–30 (1999).

J–C. Dodart et al, "The β–Amyloid Precursor Protein and its Derivatives: from Biology to Learning and Memory Processes", Reviews in the Neurosciences, 11(2–3):75–93 (2000).

D. Small et al, "Alzheimer's Disease and the Amyloid β Protein: What is the Role of Amyloid?", Journal of Neurochemistry, 73(2):443–449 (Aug., 1999).

J. Näslund et al, "Correlation Between Elevated Levels of Amyloid β–Peptide in the Brain and Cognitive Decline", JAMA, 283(12):1571–1577 (Mar., 2000).

Q–X. Li et al, "The Amyloid Precursor Protein of Alzheimer Disease in Human Brain and Blood", Journal of Leukocyte Biology, 66:567–574 (Oct., 1999).

S. Wagner et al, "Modulation of Amyloid β Protein Precursor Processing as a Means of Retarding Progression of Alzheimer's Disease", The Journal of Clinical Investigation, 104(10):1329–1332 (Nov., 1999).

Y. Han et al, "Total Asymmetric Synthesis of Highly Constrained Amino Acids β–Isopropyl–2',6'–Dimethyl–Tyrosines", Tetrahedron Letters, 38(29):5135–5138 (1997).

M. Findeis et al, "Modified–Peptide Inhibitors of Amyloid β–Peptide Polymerization", Biochemistry, 38(21):6791–6800 (May, 1999).

* cited by examiner

PRODUCTION OF CHIRALLY PURE α-AMINO ACIDS AND N-SULFONYL α-AMINO ACIDS

CROSS-REFERENCE TO RELATED APPLICATIONS

This application is a continuation-in-part of U.S. patent application Ser. No. 10/014,304, filed Dec. 11, 2001, allowed, which claims the benefit of the priority of U.S. Provisional Patent Application No. 60/255,105, filed Dec. 13, 2000.

BACKGROUND OF THE INVENTION

This invention relates to a novel process of producing chirally pure α-amino acids and N-sulfonyl α-amino acids. Compounds of the present invention are useful for a variety of purposes, including for use in pharmaceutical compositions.

A variety of techniques have been described for production of a preferred enantiomer from α-amino acids. More efficient means for producing chirally pure target compounds are needed.

SUMMARY OF THE INVENTION

In one aspect, the present invention comprises a process for preparing chirally pure S-enantiomers α-amino acids.

In a further aspect, a process is provided for preparing chirally pure S-enantiomers of 2-aminoalcohols, aldehydes and oximes.

In yet another aspect, a process is provided for preparing chirally pure S-enantiomers of N-sulfonyl a-amino acids.

In a further aspect, a process is provided for preparing chirally pure N-sulfonyl 2-aminoalcohols, aldehydes and oximes.

These and other aspects of the invention will be apparent to one of skill in the art upon reading of the following detailed description of the invention.

DETAILED DESCRIPTION OF THE INVENTION

In one aspect, the present invention is directed to a process for the preparation of chiral α-amino acids.

In another aspect, the present invention provides a process for the resolution of chiral N-sulfonyl α-amino acids.

Both processes of the invention produce chirally pure compounds which can be converted to suitable target compounds, including the corresponding 2-aminoalcohols or N-sulfonyl 2-aminoalcohols, aldehydes and oximes, among other desirable target compounds.

As used herein, the term "chirally pure" refers to compounds which are in 100% S-enantiomeric form as measured by chiral high performance liquid chromatography (HPLC). Other methods of measuring chiral purity include conventional analytical methods, including specific rotation, and conventional chemical methods. However, the technique used to measure chiral purity is not a limitation on the present invention.

As used herein, the term "pharmaceutically useful" refers to compounds having a desired biological effect, whether as a therapeutic, immune stimulant or suppressant, adjuvant, or vaccinal agent. Similarly, a variety of compounds which are suitable for use in non-pharmaceutical applications, e.g., a diagnostic, a marker, among others may be produced by the method of the invention. However, other pharmaceutically useful compounds may be produced by this method.

The compounds produced by the present invention and any target compounds into which they are converted can be used in the form of salts derived from pharmaceutically or physiologically acceptable acids or bases. These salts include, but are not limited to, the following salts with organic and inorganic acids such as acetic, lactic, citric, tartaric, succinic, fumaric, maleic, malonic, mandelic, mallic, hydrochloric, hydrobromic, phosphoric, nitric, sulfuric, methanesulfonic, toluenesulfonic and similarly known acceptable acids, and mixtures thereof. Other salts include salts with alkali metals or alkaline earth metals, such as sodium (e.g., sodium hydroxide), potassium (e.g., potassium hydroxide), calcium or magnesium.

These salts, as well as other compounds produced by the method of the invention may be in the form of esters, carbamates and other conventional "pro-drug" forms, which, when administered in such form, convert to the active moiety in vivo. In one desirable embodiment, the prodrugs are esters. See, e.g., B. Testa and J. Caldwell, "Prodrugs Revisited: The "Ad Hoc" Approach as a Complement to Ligand Design", Medicinal Research Reviews, 16(3):233–241, ed., John Wiley & Sons (1996).

Both natural and unnatural α-amino acids, natural and unnatural 2-aminoalcohols, and intermediates thereof, may be prepared according to the present invention. Typically, α-amino acids are characterized by the formula $(NH_2)(CHR)(COOH)$, in which R, is an aliphatic radical. The a-amino acids prepared according to the invention can be converted to N-sulfonyl α-amino acids and other desired compounds. Such other desired compounds include, without limitation, the corresponding 2-aminoalcohols, aldehydes, oximes, and pharmaceutically acceptable salts, hydrates, and prodrugs thereof. Similarly, both natural and unnatural N-sulfonyl α-amino acids, natural and unnatural N-sulfonyl 2-aminoalcohols, and intermediates thereof, may be prepared according to the present invention. Thus, the N-sulfonyl α-amino acids described herein can be readily reduced to 2-aminoalcohols, or converted to the corresponding aldehydes, oximes, and pharmaceutically acceptable salts, hydrates, and prodrugs thereof, using techniques known to those of skill in the art.

For example, chirally pure a-amino acids produced according to the method of the invention and having the formula $(R)_2CH(CH_2)_nCH(CO_2H)NH\text{-}R'$ can readily be converted to chirally pure 2-aminoalcohols. In another example, chirally pure N-sulfonyl α-amino acids produced according to the invention and having the formula $(R)_2CH(CH_2)_nCH(CO_2H)NH\text{—}S(O)_2R'$ are readily converted to N-sulfonyl 2-aminoalcohols of the formula $(R)_2CH(CH_2)_nCH(CH_2OH)NH_2R'$. Suitably, in the above formulae, n is 0 to about 10; R is lower alkyl, substituted lower alkyl, lower alkenyl, substituted lower alkenyl, lower alkynyl, substituted lower alkynyl, cycloalkyl, substituted cycloalkyl, phenyl, substituted phenyl, benzyl, substituted benzyl, $CH_2$cycloalkyl, $CH_2$-3-indole, CH(loweralkyl)-2-furan, CH(loweralkyl)-4-methoxyphenyl, CH(loweralkyl)phenyl, or $CH(OH)$-4-$SCH_3$-phenyl; and R' is selected from among H, lower alkyl, substituted lower alkyl, lower alkenyl, substituted lower alkenyl, lower alkynyl, substituted lower alkynyl, heterocycle, substituted heterocycle, phenyl, substituted phenyl, benzyl, substituted benzyl, cycloalkyl, and substituted cycloalkyl, among other suitable groups. In another example, an N-sulfonyl 2-aminoalcohol having the formula $(R)_2CH(CH_2)_nCH(CH_2OH)NH\text{—}S(O)_2\text{-}2\text{-}C_4H_2S\text{-}5\text{-}Cl$ is prepared using the method of the invention. However, the chirally pure compounds produced by the methods of the present invention are not limited by the above formulae.

The term "alkyl" is used herein to refer to both straight- and branched-chain saturated aliphatic hydrocarbon groups having one to ten carbon atoms, preferably one to eight carbon atoms and, most preferably, one to six carbon atoms; as used herein, the term "lower alkyl" refers to straight- and branched-chain saturated aliphatic hydrocarbon groups having one to six carbon atoms; "alkenyl" is intended to include both straight- and branched-chain alkyl group with at least one carbon—carbon double bond and two to eight carbon atoms, preferably two to six carbon atoms; "alkynyl" group is intended to cover both straight- and branched-chain alkyl groups with at least one carbon—carbon triple bond and two to eight carbon atoms, preferably two to six carbon atoms.

The terms "substituted alkyl", "substituted alkenyl", and "substituted alkynyl" refer to alkyl, alkenyl, and alkynyl as just described having from one to three substituents selected from the group including halogen, CN, OH, $NO_2$, amino, aryl, heterocyclic, substituted aryl, substituted heterocyclic, alkoxy, substituted alkoxy, aryloxy, substituted alkyloxy, alkylcarbonyl, alkylcarboxy, alkylamino, and arylthio. These substituents may be attached to any carbon of an alkyl, alkenyl, or alkynyl group provided that the attachment constitutes a stable chemical moiety.

The term "aryl" is used herein to refer to a carbocyclic aromatic system, which may be a single ring, or multiple aromatic rings fused or linked together as such that at least one part of the fused or linked rings forms the conjugated aromatic system. The aryl groups include, but are not limited to, phenyl, naphthyl, biphenyl, anthryl, tetrahydronaphthyl, phenanthryl, and indane.

The term "substituted aryl" refers to aryl as just defined having one to four substituents from the group including halogen, CN, OH, $NO_2$, amino, alkyl, cycloalkyl, alkenyl, alkynyl, alkoxy, aryloxy, substituted alkyloxy, alkylcarbonyl, alkylcarboxy, alkylamino, and arylthio.

The term "substituted benzyl" refers to a benzyl (Bn) group, having substituted on the benzene ring, one to five substituents from the group including halogen, CN, OH, $NO_2$, amino, alkyl, cycloalkyl, alkenyl, alkynyl, alkoxy, aryloxy, substituted alkyloxy, alkylcarbonyl, alkylcarboxy, alkylamino, and arylthio.

The term "heterocyclic" is used herein to describe a stable 4- to 7-membered monocyclic or a stable multicyclic heterocyclic ring which is saturated, partially unsaturated, or unsaturated, and which consists of carbon atoms and from one to four heteroatoms selected from the group including N, O, and S atoms. The N and S atoms may be oxidized. The heterocyclic ring also includes any multicyclic ring in which any of above defined heterocyclic rings is fused to an aryl ring. The heterocyclic ring may be attached at any heteroatom or carbon atom provided the resultant structure is chemically stable. Such heterocyclic groups include, for example, tetrahydrofuran, piperidinyl, piperazinyl, 2-oxopiperidinyl, azepinyl, pyrrolidinyl, imidazolyl, pyridyl, pyrazinyl, pyrimidinyl, pyridazinyl, oxazolyl, isoxazolyl, morpholinyl, indolyl, quinolinyl, thienyl, furyl, benzofuranyl, benzothienyl, thiamorpholinyl, thiamorpholinyl sulfoxide, isoquinolinyl, and tetrahydrothiopyran.

The term "substituted heterocyclic" is used herein to describe the heterocyclic just defined having one to four substituents selected from the group which includes halogen, CN, OH, $NO_2$, amino, alkyl, substituted alkyl, cycloalkyl, substituted cycloalkyl, alkenyl, substituted alkenyl, alkynyl, substituted alkynyl, alkoxy, substituted alkoxy, aryloxy, substituted aryloxy, alkyloxy, substituted alkyloxy, alkylcarbonyl, substituted alkylcarbonyl, alkylcarboxy, substituted alkylcarboxy, alkylamino, substituted alkylamino, arylthio, or substituted arylthio.

The term "substituted cycloalkyl" is used herein to describe a carbon-based ring having more than 3 carbon-atoms which forms a stable ring and having from one to five substituents selected from the group consisting of halogen, CN, OH, $NO_2$, amino, alkyl, substituted alkyl, alkenyl, substituted alkenyl, alkynyl, alkoxy, aryloxy, substituted alkyloxy, alkylcarbonyl, alkylcarboxy, alkylamino, substituted alkylamino, arylthio, heterocyclic, substituted heterocyclic, aminoalkyl, and substituted aminoalkyl.

Where the terms "substituted alkylcycloalkyl", "substituted alkylOBn", "substituted alkylpyridyl", "substituted alkylfuranyl", "substituted alkyl $NHR_7$", and phenyl (substituted)alkyl, "substituted alkylOH", and "substituted alkyl$SR_8$" are recited in Formula I and Formula Ia below, the substitution may occur at the alkyl group or on the corresponding base compound.

As used in the definition of the $R_4$ group in Formula I and Ia below, an N-substituted piperidinyl group may be defined as a substituted heterocyclic group. Among particularly desirable substituents are N-alkyl-, N-aryl-, N-acyl-, and N-sulfonyl piperidinyl groups. One particularly suitable N-acyl-piperidinyl group is N-t-butyloxycarbonyl (BOC)-piperidine. However, other suitable substituents can be readily identified by one of skill in the art.

The term "alkoxy" is used herein to refer to the O(alkyl) group, where the point of attachment is through the oxygen-atom and the alkyl can be optionally substituted. The term "aryloxy" is used herein to refer to the O(aryl) group, where the point of attachment is through the oxygen-atom and the aryl can be optionally substituted. The term "alkylcarbonyl" is used herein to refer to the CO(alkyl) group, where the alkyl can be optionally substituted and the point of attachment is through the carbon atom of the carbonyl group and the. The term "alkylcarboxy" is used herein to refer to the COO(alkyl) group, where the alkyl can be optionally substituted and the point of attachment is through the carbon atom of the carboxy group. The term "aminoalkyl" refers to both secondary and tertiary amines wherein the alkyl or substituted alkyl groups, containing one to eight carbon atoms, which may be either same or different, and the point of attachment is on the nitrogen atom.

The term "halogen" refers to Cl, Br, F, or I.

The term "ring" structure, e.g., when $R_3$ and $R_4$ may form a ring structure in Formula Ia, includes a monocyclic structure, a bridged cyclo structure, and fused cyclo structures, unless the type of ring structure is otherwise specified.

The term "strong non-nucleophilic base" refers to a non-nucleophilic basic reagent, which does not act as a nucleophile or bind to the reagents utilized according to the reaction. A number of non-nucleophilic bases are known in the art and include sodium hydride, potassium hydride, lithium diisopropylamide and potassium hexamethyldisilazide.

The term "aqueous base" refers to a solution composed of, at a minimum, a base and water. A number of bases which readily dissolve in water are known in the art and include alkali metal hydroxides such as lithium hydroxide, sodium hydroxide or potassium hydroxide, among others. The aqueous base solution may further contain other reagents which do not interfere with the reactions of the present invention, and include organic solvents such as tetrahydrofuran, methanol, ethanol, or hydrocarbon solvents, salts such as sodium chloride, and buffers, among others.

The term "aqueous acid" refers to a solution composed of, at a minimum, an acid and water. The aqueous acid solution may further contain other reagents which do not interfere with the reactions of the present invention.

The term "strong acid" or "strong base" refers to an acid or base that is completely ionized in solution. Common strong acids include HCl, HBr, HI, $HNO_3$, $H_2SO_4$, and $HClO_4$. Common strong bases include hydroxides of the alkali metals (Li, Na, K, Rb, Cs) and hydroxides of the heavy alkaline earths (Ca, Sr, Ba).

The term "inorganic" acid or "inorganic" base includes acids and bases which do not contain carbon.

The term "organic solvent" may include any carbon-containing solvent known in the art, which does not react with the reagents utilized in the reaction and includes saturated hydrocarbon solvents, unsaturated hydrocarbon solvents, including aromatic hydrocarbon solvents, alcohols, halocarbons, ethers, and acetates, among others.

Synthesis of Chirally Pure Compounds

The chirally pure compounds can be prepared using the methods described below. Where reference to conventional techniques is made, one of skill in the art will be able to readily select appropriate synthetic methods and reagents, which are known in the synthetic organic arts or variations of these methods by one skilled in the art. See, generally, *Comprehensive Organic Synthesis*, "Selectivity, Strategy & Efficiency in Modern Organic Chemistry", ed., I. Fleming, Pergamon Press, New York (1991); *Comprehensive Organic Chemistry*, "The Synthesis and Reactions of Organic Compounds", ed. J. F. Stoddard, Pergamon Press, New York (1979).

Preparation of Chirally Pure α-Amino Acids

In one aspect, the invention provides a method for preparing chirally pure α-amino acids from chirally impure α-amino acids. For the preparation of chirally pure α-amino acids XXXXVI, a novel asymmetric variant of the Strecker α-amino acid synthesis is utilized (Scheme 14; *J. Org. Chem.* 54:1055–1062 (1989)). In this route (Scheme I), an aldehyde XXXXVII is reacted with a cyanide salts and α-methylbenzylamine or a salt thereof in a 1:1:1 molar ratio in a suitable solvent to afford the compound XXXVIII. Included among desirable cyanide salt are sodium cyanide and potassium cyanide. However, other suitable cyanide salts may be readily selected for use in the method of the invention. Preferably, the solvent is 1:1 methanol to water. Suitably, the reaction is performed for about 12 to about 24 hours, and most preferably, about 18 hours. However, longer or shorter reaction times may be readily utilized. Optionally, following this reaction, a suspension containing precipitate is formed, which is subjected to filtration and is washed (e.g., with water) to provide a powder. Compound XXXVIII is dissolved with a strong inorganic acid which is desirably cold upon combination with the compound (e.g., about 0° C. to about 10° C.) to provide the compound XXXXIX. Desirably, the strong inorganic acid is sulfuric acid. However, other strong inorganic acids may be readily selected. The reaction mixture is neutralized with an inorganic base and extracted with an organic solvent to compound XXXXIX. Suitably, extraction may utilize ethyl acetate or another suitable compound, and further involves drying and concentrating to provide compound XXXXIX. The hydrogenolysis reaction takes place in the presence of a suitable catalyst under pressure, e.g., Pd or RaNi under 3 atm pressure, filtering to remove the catalyst followed by concentration to remove solvent provides compound XXXXX. Compound XXXXX is then dissolved with an aqueous acid to afford the derivatives of formula XXXXVI. Where XXXXX has been dried to powder form, it is dissolved in a strong inorganic acid at high temperature to afford a salt of a chirally pure α-amino acid. For example, hydrochloric acid at 100° C. may be utilized. Alternatively, other acids and other suitable temperatures may be readily selected by one of skill in the art. Most desirably, the hydrolysis step is performed over a period of about 12 to 18 hours, or longer. In one suitable embodiment, the step is performed over 16 hours. Optionally, the resulting reaction mixture is concentrated to provide a product which consists of the amino acid salt and one equivalent of ammonium salt. In this example, the product is the amino acid hydrochloride salt and one equivalent of ammonium chloride. This product is dissolved in water to which the base, e.g., sodium hydroxide or ammonium hydroxide, is added to form a solution.

Scheme 1

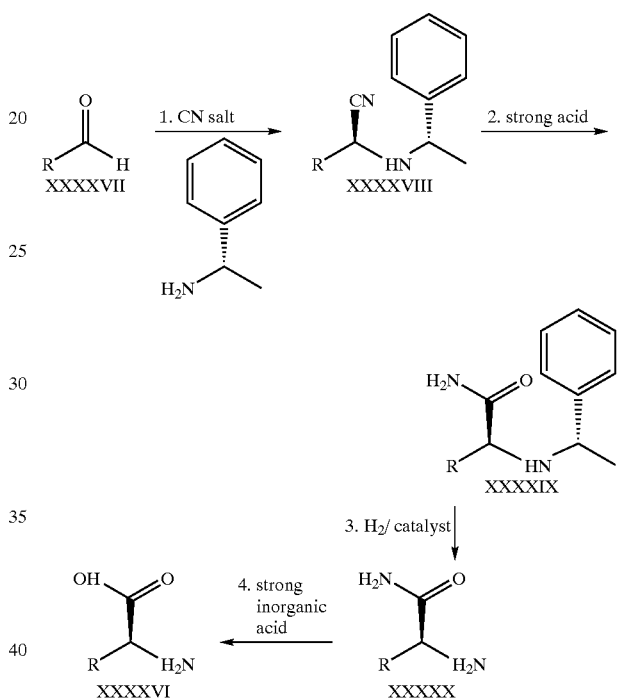

These chirally pure a-amino acids produced according to the method of the invention can be readily utilized in the form produced, or converted to a desired target compound. For example, a chirally pure a-amino acid can be readily converted to a chirally pure 2-aminoalcohol by reducing the a-amino acid to the 2-aminoalcohol and recrystallizing the 2-aminoalcohol to afford the chirally pure 2-aminoalcohol. These and other uses for the chirally pure a-amino acids of the invention will be readily apparent to those of skill in the art from the information provided herein and that known to those of skill in the art.

Preparation of Chirally Pure N-Sulfonyl α-Amino Acids

In another aspect, the invention provides a scheme for resolving a chirally impure N-sulfonyl α-amino acid having a β-branched alkyl substituent to provide a chirally pure N-sulfonyl α-amino acid. Desirably, the N-sulfonyl α-amino acid is N-sulfonyl β-ethylnorvaline. In another embodiment, the norvaline compound can be substituted with a compound selected from among N-sulfonyl β-ethylnorvaline, N-sulfonylvaline, and N-sulfonyl β-n-propylnorleucine. Alternatively, one of skill in the art may use the method of the invention with another selected N-sulfonyl a-amino acid having a β-branched alkyl substituent for preparing the corresponding chirally pure compound.

Suitably, N-sulfonyl β-ethylnorvaline (or another selected compound) is mixed with chirally pure ephedrine hemihydrate in ethanol at a molar ratio of 1:1. The mixture is then heated to dissolve the solids. In one embodiment, the mixture is heated to about 80° C. However, other suitable temperatures may be readily selected. Thereafter, the mixture is cooled in order to allow a precipitate to form. This cooling step may be performed at room temperature or at reduced temperature (e.g., about 5° C.) overnight (about 16–20 hours). The temperature and the period of the cooling step each may be adjusted upwardly or downwardly, as needed or desired. Optionally, the suspension is filtered following cooling. The salt is then recrystallized and then dissolved in a solvent and a strong aqueous acid. Suitably, the recrystallizing step is performed in boiling ethyl acetate and the recrystallized salt is separated. This may be performed using filtration or other conventional methods. Suitably, the salt is dissolved in an organic solvent and strong acid. The organic extract is washed, dried and concentrated to provide the chirally pure N-sulfonyl α-amino acid. In one embodiment, the wash step is performed with a strong aqueous acid such as, for example, hydrochloric acid, and drying is performed with sodium sulfate or the like.

Suitably, these chirally pure α-amino acids and N-sulfonyl α-amino acids are useful for a variety of purposes. For example, these chirally pure α-amino acids and N-sulfonyl α-amino acids can be converted to the corresponding N-sulfonyl 2-aminoalcohols by the methods described herein.

Thus, in one embodiment the chirally pure α-amino acids produced according to the present invention are useful in the synthesis of chiral N-sulfonyl a-amino acids. Suitable methods for preparation of these chiral N-sulfonyl 2-amino acids are provided herein.

Conversion to 2-Aminoalcohols

The processes of the invention provide efficient route to the synthesis of chirally pure S enantiomers of a-amino acids and N-sulfonyl a-amino acids which are useful in preparing 2-aminoalcohols or N-sulfonyl 2-aminoalcohols, and intermediates thereof, which are useful for a variety of purposes.

For example, the exemplary compounds provided herein, the N-sulfonyl 2-amino acids and their corresponding alcohols, aldehydes, oximes and salts, are useful for modulating α-amyloid production, which is implicated in amyloid angiopathy, cerebral amyloid angiopathy, systemic amyloidosis, Alzheimer's Disease (AD), hereditary cerebral hemorrhage with amyloidosis of the Dutch type, inclusion body myositis, Down's syndrome, among others. Thus, the compounds of Formula (I) are useful in modulating beta amyloid production in subjects at risk for, or suffering from, AD or other diseases resulting from elevated levels of beta amyloid protein in the brain. These compounds and their uses are described in more detail in co-pending U.S. patent application Ser. No. 10/014,304, filed Dec. 11, 2001, which is incorporated herein by reference. The compounds of Formula (I) include pharmaceutically acceptable salts and/or hydrates or prodrugs thereof, wherein:

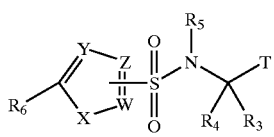

(I)

$R_3$ is selected from the group consisting of hydrogen, alkyl, and substituted alkyl;

$R_4$ is selected from the group consisting of hydrogen, alkyl, substituted alkyl, alkylcycloalkyl, substituted alkylcycloalkyl, phenyl(substituted)alkyl, alkylOH, substituted alkylOH, alkylOBn, substituted alkylOBn, alkylpyridyl, substituted alkylpyridyl, alkylfuranyl, substituted alkylfuranyl, CH(OH)phenyl, CH(OH) substituted phenyl, alkenyl, substituted alkenyl, cycloalkyl, substituted cycloalkyl, N-substituted-piperidinyl, piperidinyl, substituted piperidinyl, tetrahydrothiopyran, substituted tetrahydrothiopyran, 2-indane, substituted 2-indane, phenyl, substituted phenyl, alkylNHR$_7$, and substituted alkylNHR$_7$;

with the proviso that $R_3$ and $R_4$ are not both hydrogen;

$R_7$ is alkyl, substituted alkyl, cycloalkyl, substituted cycloalkyl, benzyl, substituted benzyl, alkylOH, substituted alkylOH, alkylSR$_8$, or substituted alkylSR$_8$;

$R_8$ is alkyl, substituted alkyl, benzyl, or substituted benzyl;

or $R_3$ and $R_4$ may be joined to form a ring;

$R_5$ is selected from the group consisting of hydrogen, lower alkyl, substituted lower alkyl, alkenyl, substituted alkenyl, alkynyl, substituted alkynyl, CH$_2$cycloalkyl, substituted CH$_2$Cycloalkyl, benzyl, substituted benzyl, and CH$_2$CH$_2$QR$_9$;

Q is O, NH or S;

$R_9$ is lower alkyl, substituted lower alkyl, phenyl, or substituted phenyl;

$R_6$ is selected from the group consisting of hydrogen, halogen and CF$_3$;

T is selected from the group consisting of

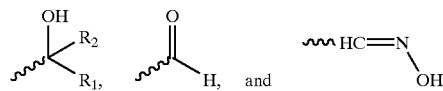

$R_1$ and $R_2$ are independently selected from the group consisting of hydrogen, alkyl, substituted alkyl, CF$_3$, alkenyl, substituted alkenyl, alkynyl, substituted alkynyl, cycloalkyl, substituted cycloalkyl, phenyl, substituted phenyl, and (CH$_2$)$_n$ (1,3)dioxane, where n is 2 to 5;

W, Y and Z are independently selected from the group consisting of C, CR$_{10}$ and N, with the proviso that at least one of W, Y and Z must be C;

$R_{10}$ is selected from the group consisting of hydrogen and halogen;

X is selected from the group consisting of O, S, SO$_2$, and NR$_{11}$;

$R_{11}$ is selected from the group consisting of hydrogen, lower alkyl, substituted lower alkyl, benzyl, substituted benzyl, phenyl, and substituted phenyl;

provided that when the compound contains one or more chiral centers, at least one of the chiral centers must be of S-stereochemistry.

The point of attachment of the W-X-Y-Z-C heterocyclic ring to the SO$_2$ group is not a limitation of the present invention. However, in one preferred embodiment, the ring is attached to the SO$_2$ group through a carbon-atom. However, the ring may be attached through O, S, or N heteroatoms.

The compounds of formula (I) contain one or more asymmetric carbon atoms and some of the compounds may contain one or more asymmetric (chiral) centers and may thus give rise to optical isomers and diastereomers. While shown without respect to stereochemistry in Formula (I), when the compounds of Formula (I) contain one or more chiral centers, at least one of the chiral centers is of S-stereochemistry. Most preferably, the carbon atom to which N, T, $R_3$ and $R_4$ are attached is of S-stereochemistry.

In one embodiment, the present invention is directed toward a process for preparing chiral S enantiomers of N-sulfonyl 2-aminoalcohols of the general formula Ia:

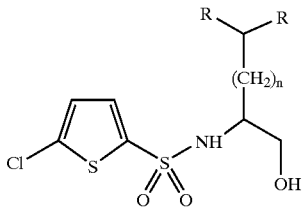

wherein R is lower alkyl, substituted lower alkyl, lower alkenyl, substituted lower alkenyl, lower alkynyl, substituted lower alkynyl, cycloalkyl, substituted cycloalkyl, phenyl, substituted phenyl, benzyl, substituted benzyl, $CH_2$cycloalkyl, $CH_2$-3-indole, CH(loweralkyl)-2-furan, CH(loweralkyl)-4-methoxyphenyl, CH(loweralkyl)phenyl, or CH(OH)-4-$SCH_3$-phenyl and n is 0 to about 10.

Desirably, the compounds prepared according to the method of the invention contain at least one chiral carbon center, where R in the above-noted structures is the same. In certain desired embodiments, the R groups are methyl, ethyl, and n-propyl, and most preferably the R groups are ethyl. However, the invention further encompasses producing α-amino acids and 2-aminoalcohols of the general formulae provided herein where the R groups are different. In these compounds one or more additional chiral centers may be present; however, the additional chiral centers must be optically pure and must not interfere with the production of the chirally pure α-amino acids, 2-aminoalcohols, and pure S enantiomers of N-sulfonyl 2-aminoalcohols of the present invention.

In another preferred embodiment, the chiral carbon center is of S-stereochemistry which gives rise to enantiomerically pure products.

In one embodiment, the method of the invention is used to produce chirally pure α-amino acids which are readily converted to the N-sulfonyl α-amino acids. For example, a chirally pure α-amino acids prepared according to the invention can be used to prepare a compound Formula (I). Particularly desirable compounds of Forula (I) include thiophenesulfonamides, and more desirably, 5-halo thiophenesulfonamides, and most desirably, 5-halo thiophene sulfonamides with β-branches in the side chain of a primary alcohol. Thus, with respect to Formula (I), the compound produced by the invention desirably has a structure in which X is S, W is C (or $CR_{10}$), Y is C (or $CR_{10}$) and Z is C (or $CR_{10}$), and the sulfonamide is attached to C2 of the thiophene ring. More desirably, X is S, W is C (or $CR_{10}$), Y is C (or $CR_{10}$), Z is C (or $CR_{10}$) and $R_6$ is a halogen. Most desirably, X is S, W is C, Y is C, Z is C, $R_6$ is a halogen, T is C(OH)$R_1R_2$, where $R_1$ and $R_2$ are hydrogen, $R_3$ is H, $R_4$ is a lower alkyl of S-stereochemistry, and $R_5$ is H. Other desirable compounds of Formula (I) are furansulfonamides, in which X is O, W is C, Y is C, and Z is C. In one particularly desirable embodiment, the furansulfonamides of Formula (I) are further characterized by β-branches in the side chain of a primary alcohol. Thus, with respect to Formula (I), in these compounds T is C(OH)$R_1R_2$, in which $R_1$ and $R_2$ are hydrogen, $R_3$ is H, $R_4$ is a lower alkyl of S-stereochemistry, $R_5$ is H and $R_6$ is halogen. In preliminary screening assays in vitro and in vivo, selected compounds of these structures have been found to have unexpectedly good beta-amyloid inhibitory activity, and in many cases, better activity than compounds of Formula (I) having other heterocycles (e.g., furans, where X is O). However, other such compounds of Formula (I) are also useful for the purposes described herein.

Additionally, other chirally pure a-amino acids and N-sulfonyl a-amino acids prepared by the invention can be converted to the desired N-sulfonyl 2-aminoalcohols, which include the compounds of Formula (I). The compounds of Formula (I) are characterized by being sulfonamides of Formula (I), which have β-branches in the side chain of the primary alcohol group. Thus, with respect to Formula (I), in these compounds T is C(OH)$R_1R_2$, $R_1$ and $R_2$ are hydrogen, $R_3$ is H, $R_4$ is a lower alkyl of S-stereochemistry, and $R_5$ is H. These and other chirally pure N-sulfonyl α-amino acids can be prepared following the methods described herein.

A first method of preparation consists of reaction of a 2-aminoalcohol II with the appropriate sulfonyl halide in the presence of a base such as triethylamine (TEA) and in a suitable solvent to afford compounds of Formula III. For compounds where $R_2$ and $R_1$ are hydrogen, oxidation of the N-sulfonyl primary alcohol with pyridinium chlorochromate (PCC) or under Swern conditions then affords the corresponding aldehyde IV which can be reacted with Grignard reagents (RMgX, where R is an organic radical and X is a halogen) to afford the secondary alcohols V as a mixture of diastereomers which can be separated by high performance liquid chromatography (HPLC) (Scheme 2).

Scheme 2

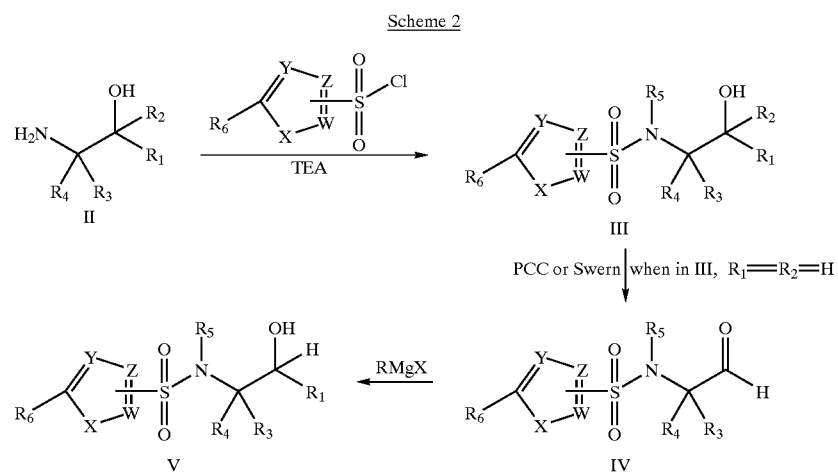

A second method of preparation involves reaction of an α-amino acid or ester IX with the appropriate sulfonyl halide in the presence of a base such as triethylamine and in a suitable solvent to afford compounds of Formula X (Scheme 3). The intermediate N-sulfonyl ester X (Rx=H) can be converted to the corresponding primary alcohol VIII (R$_1$=R$_2$=H) utilizing standard methodology such as LiAlH$_4$, B$_2$H$_6$ or cyanuric chloride/NaBH$_4$. The intermediate N-sulfonyl ester X (Rx=alkyl, Bn) can also be reduced to the corresponding primary alcohol VIII (R$_1$=R$_2$=H) utilizing standard methodology such as LiAlH$_4$. Alternatively, the intermediate N-sulfonyl ester X (Rx=alkyl, Bn) can be converted to the aldehyde IV with DiBAL.

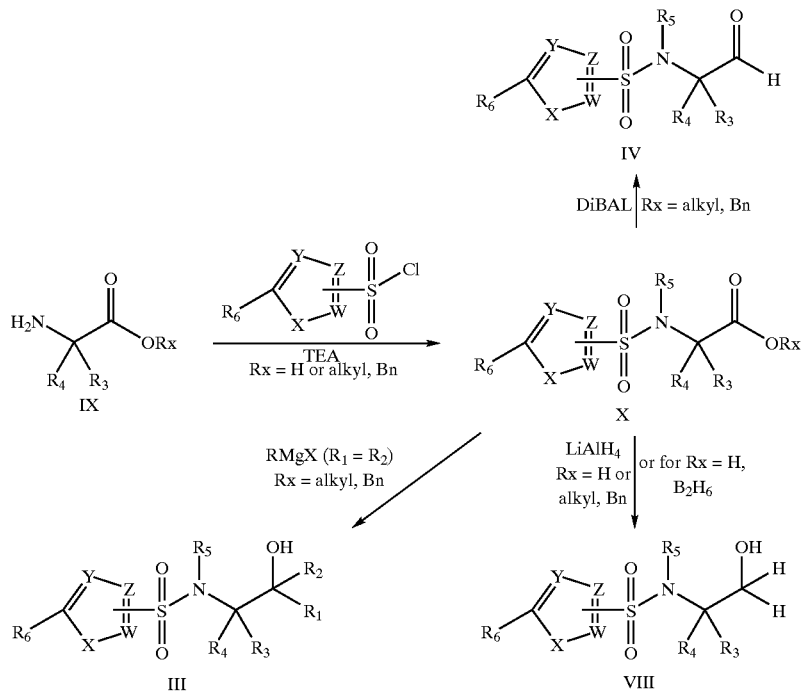

Scheme 3

Finally, the intermediate N-sulfonyl ester X (Rx=alkyl, Bn) can be reacted with 2 equivalents of Grignard reagent to afford the tertiary alcohols III with R$_1$=R$_2$. Alternatively, for tertiary alcohols III with R$_1$ not equal to R$_2$, the corresponding Weinreb amide (see Scheme 11) of the N-sulfonyl acid can be prepared and subsequently reacted with R$_1$MgX and R$_2$MgX. For compounds of formula X (Rx=H) that have an asymmetric center at the a-amino acid carbon, the pure enantiomers can be obtained by standard resolution procedures employing recrystallization of salts formed with various chiral bases.

In a variation of the second method to prepare the primary alcohols, an α-amino acid or ester (or N-protected derivative thereof) VI is first converted to the corresponding primary 2-aminoalcohol VII (using the methodology outlined in the previous paragraph), which is subsequently, after deprotection (if necessary), reacted with the appropriate sulfonyl halide (Scheme 4) to afford compounds of Formula VIII.

Scheme 4

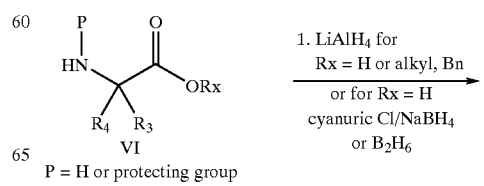

P = H or protecting group

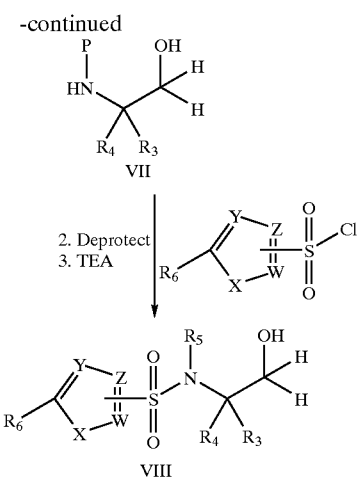

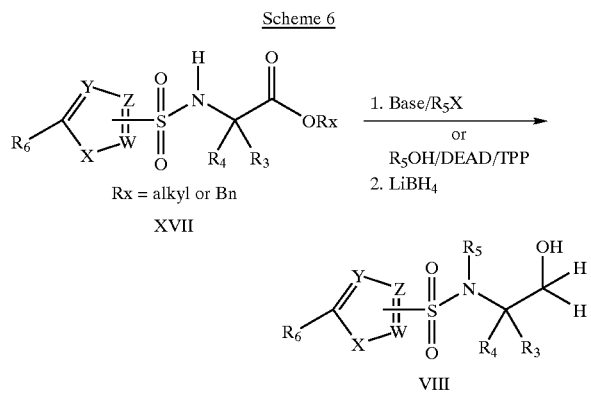

For preparation of compounds derived from unnatural α-amino acids containing beta branching in the amino acid side chain, a method of preparation based on the work of Hruby (*Tet. Lett.* 38: 5135–5138 (1997)) is outlined in Scheme 5. This route entails formation of the α,β-unsaturated amide XII of the Evans chiral auxiliary from an α, β-unsaturated acid XI, followed by conjugate addition of an organocuprate, trapping of the resulting enolate anion XIII with N-bromosuccinimide (NBS), displacement of the bromide XIV with azide anion (provided by tetramethylguanidinium azide (TMGA)) to afford XV, followed by reduction to the 2-aminoalcohol and subsequent sulfonylation to afford the target compound XVI. In Schemes 2 through 5, $R_5$ is H.

For the preparation of N-alkylated sulfonamides VIII ($R_5$=alkyl etc.), the sulfonamide ester XVII can be N-alkylated by either treatment with a suitable base such as potassium carbonate followed by the alkylating agent $R_5X$ or by employing Mitsunobu conditions ($R_5$OH/DEAD, TPP). LiBH$_4$ reduction of the N-alkylated sulfonamide ester affords the N-alkylated sulfonamide in the primary alcohol series VIII (Scheme 6). These primary alcohols VIII can be converted to the secondary alcohols V or aldehyde IV series by chemistry that has been outlined above. Alternatively, the N-alkylated sulfonamide esters, or their corresponding Weinreb amides, can be treated with Grignard reagents to afford the N-alkylated tertiary alcohols III.

When the heterocycle attached to the sulfonamide in the above alcohols is thiophene, the corresponding sulfone derivative XIX may be obtained by oxidation of the thiophene compound XVIII with MCPBA (Scheme 7).

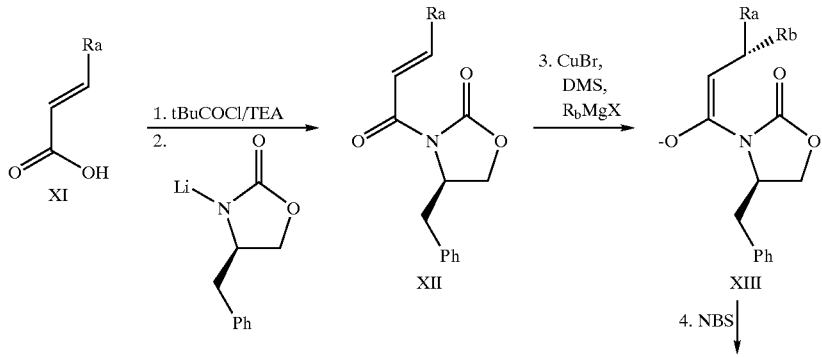

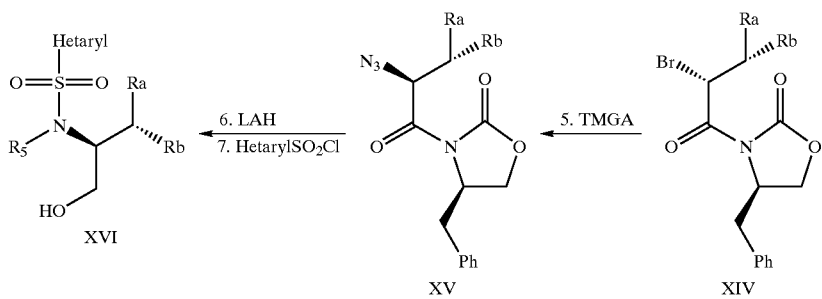

Scheme 7

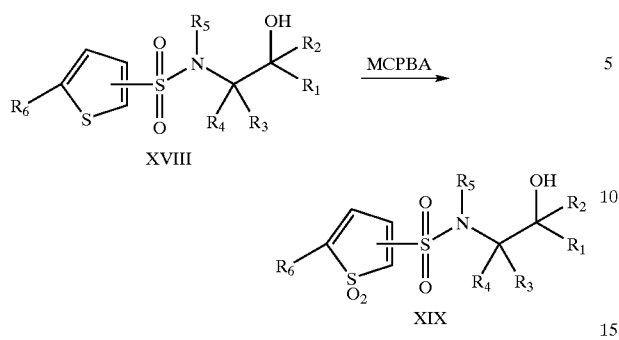

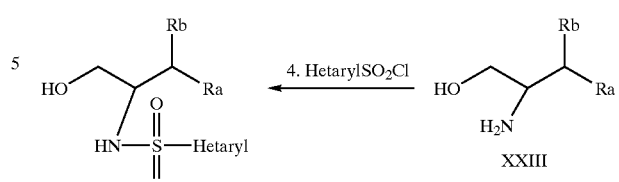

An alternate preparation of sulfonamides derived from unnatural 2-aminoalcohols utilizes the Bucherer modification of the Strecker α-amino acid synthesis (Scheme 8). In this route, an aldehyde XX is reacted with cyanide anion and ammonium carbonate to afford the hydantoin XXI, which is hydrolyzed to the α-amino acid XXII. This compound is then reduced to XXIII and sulfonylated to afford the desired compounds of Formula XXIV.

For sulfonamides derived from 2-aminoalcohols containing an N or O heteroatom in the side chain, a route has been devised starting from D-serine (Scheme 9). In this route, D-serine XXV is first sulfonylated to XXVI and subsequently converted to the ketone XXVII, which is reductively aminated to the target compounds of Formula XXVIII.

For sulfonamides derived from 2-aminoalcohols in the secondary alcohol series with $R_1$=H and $R_2$=$CF_3$ (compound XXIX), a method of preparation has been devised that is outlined in Scheme 10 starting from the aldehyde IV (prepared as in Scheme 2).

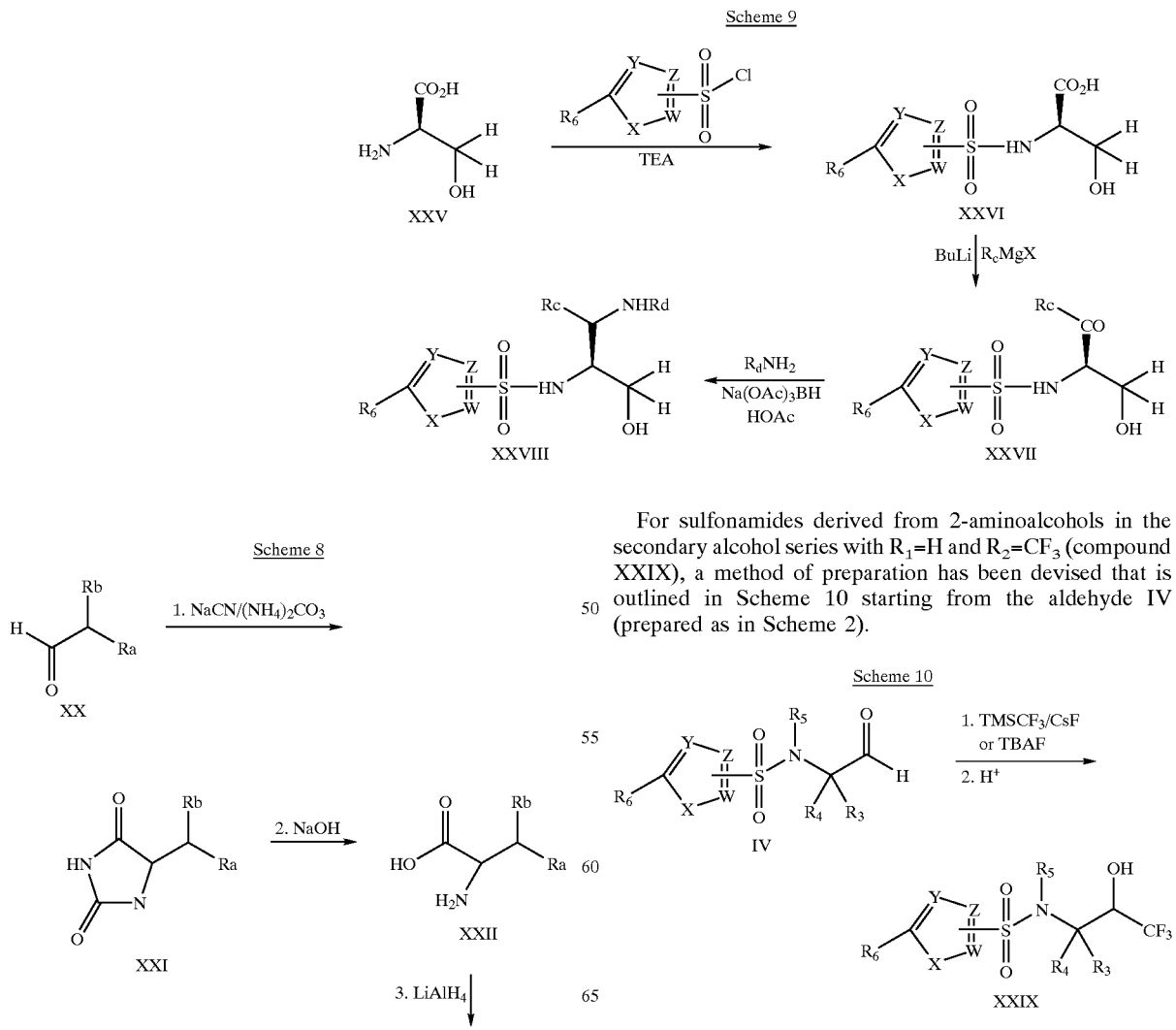

As has been mentioned in the section concerning Scheme 2, the preparation of sulfonamides derived from 2-aminoalcohols in the secondary alcohol series V results in the formation of a diastereomeric mixture. An alternate method of preparation of these compounds that results in the production of a pure diastereomer is outlined in Scheme 11 for compounds derived from L-isoleucine. This method, which utilizes chemistry previously employed by Roux (*Tetrahedron* 50: 5345–5360 (1994)), consists of addition of Grignard reagents to the Weinreb amide XXX (derived from the requisite α-amino acid) followed by stereo specific reduction of the ketone XXXI to afford a single diastereomeric N-protected 2-aminoalcohol XXXII. Deprotection of this compound followed by reaction with sulfonyl chlorides affords the pure diastereomeric sulfonamide secondary alcohols of Formula XXXIII.

Scheme 11

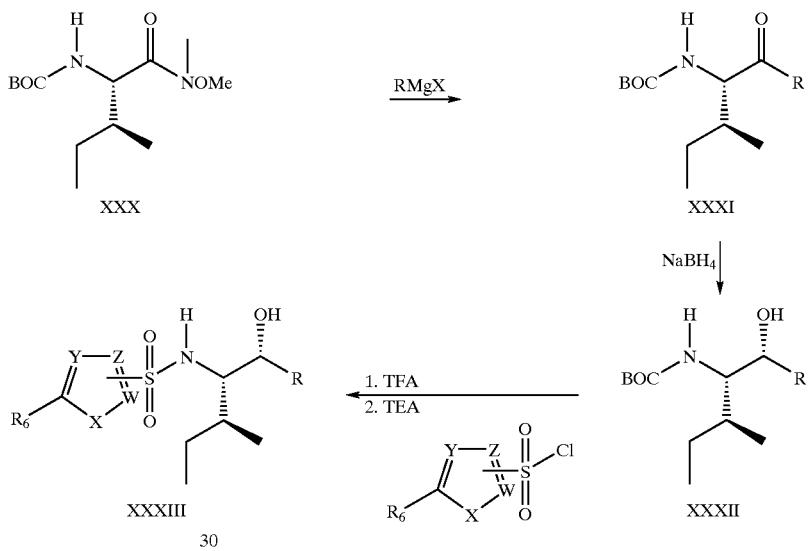

When the heterocycle attached to the sulfonamide in the above alcohols is thiophene, the corresponding 5-iodo and 5-fluoro-thiophene derivatives may be obtained by conversation of the 5-bromo-thiophene derivative XXXIV (obtained as in Scheme 2) to a 5-trialkyltin-thiophene intermediate XXXV which can be converted to either the 5-iodo-thiophene (XXXVII) by treatment with sodium iodide and chloramine T or the 5-fluoro-thiophene analog (XXXVI) by treatment with SELECTFLUOR™ (Aldrich Chemical Co) (Scheme 12).

Scheme 12

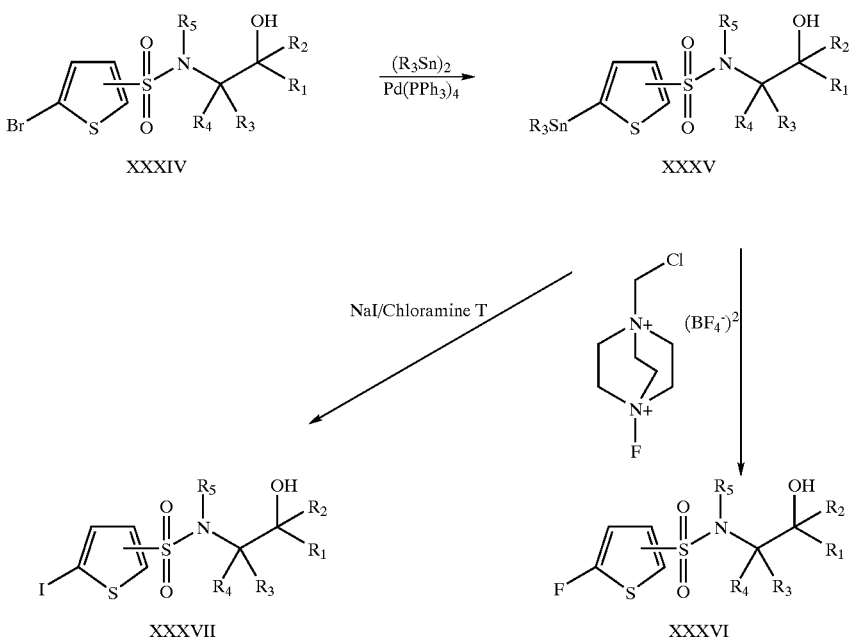

Sulfonamides derived from cyclohexylglycinol substituted by alkoxy and amino groups at the 4 position of the cyclohexane ring can be prepared according to the methods described herein (Scheme 13). This route entails initial hydrogenation of 4-L-hydroxyphenylglycine XXXVIII, followed by sulfonylation, reduction of the carboxylic acid with diborane and formation of the N,O-acetonide XXXIX. The 4-hydroxy acetonide XXXIX is then O-alkylated using sodium hydride and an alkylating agent such as an alkyl or benzyl bromide. This is followed by removal of the protecting group by treatment with aqueous acid to afford the 4-ether derivatives of Formula XXXX. Alternatively, the 4-hydroxy acetonide XXXIX can be oxidized to the 4-ketone which can be reductively aminated and deprotected to afford the corresponding 4-amino analogs of Formula XXXXI.

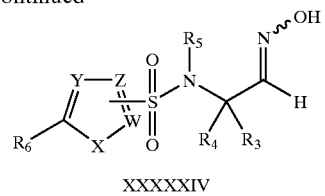

XXXXXIV

EXAMPLES

The following examples are provided to illustrate the production of representative compounds according to the method of the invention. One skilled in the art will appreciate that although specific reagents and conditions are outlined in the following examples, these reagents and conditions are not a limitation on the present invention.

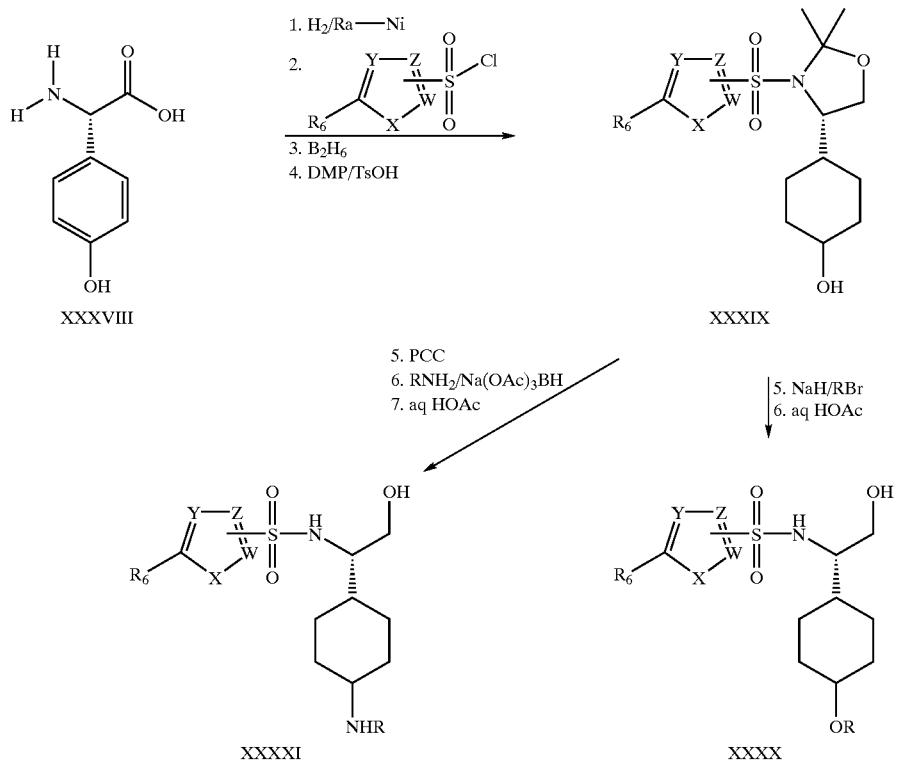

Where desired, oximes XXXXXIV can be derived from the corresponding aldehydes IV by standard methodology as depicted in Scheme 14.

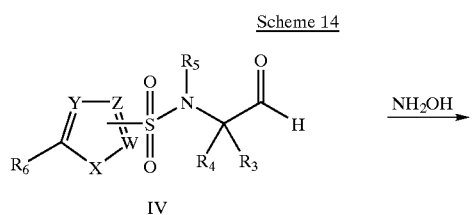

Example 1

Method 1

5-Chloro-N-[(S)-2-ethyl-1-formylbutyl]thiophene-2-sulfonamide

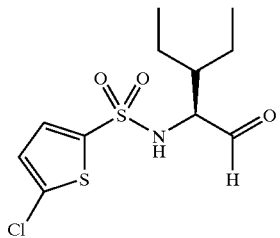

A. 5-(1-Ethyl-propyl)-imidazolidine-2,4-dione

Sodium cyanide (12.0 g, 244.8 mmol) and 2-ethylbutyraldehyde (10.0 mL, 81.3 mmol) were added to ammonium carbonate (25.4 g, 325.3 mmol) in $H_2O$ (300 mL). Ethanol (300 mL) was added and salts precipitated. The reaction mixture was heated to 90° C. After 1 h, the mixture became homogeneous and was stirred at 90° C. for 18 h. After cooling to 25° C., about 500 mL of solvent was removed in vacuo. Concentrated HCl was added to acidify the mixture to pH 1–2 and a precipitate formed. It was filtered and the precipitate was recrystallized from EtOAc to afford 5-(1-ethyl-propyl)-imidazolidine-2,4-dione as a white solid (12.9 g, 93%). Mass Spectrum (−ESI): 169 (M−H)⁻.

B. N-[(5-Chloro-2-thienyl)sulfonyl]-3-ethylnorvaline 5-(1-Ethyl-propyl)-imidazolidine-2,4-dione (12.3 g, 72.3 mmol) was dissolved in a 150 mL solution of aqueous NaOH (11.6 g, 289.2 mmol). The solution was heated by microwave in a sealed vessel for 1 h. (Microwave conditions: 15 min @ 100% power, 150° C., 50 psi, then 5 min 0% power, then 15 min @ 100% power, 150° C., 50 psi, then repeat sequence.) Water and ammonium hydroxide were removed from the reaction mixture in vacuo and the resulting crude amino acid and NaOH mixture was used in the next reaction without further purification.

The crude amino acid and NaOH mixture was dissolved in 300 mL of water. The mixture was cooled to 0° C. in an ice bath. 5-Chlorothiophene-2-sulfonyl chloride (17.3 g, 79.5 mmol) was dissolved in 100 mL of THF and added dropwise to the reaction mixture over 0.5 h. After 1 h the reaction mixture was allowed to warm gradually to 25° C. and stirred for 16 h. THF was removed in vacuo and then the mixture was acidified to pH 1 with 1N HCl. After about 15 min, a precipitate began to crash out of the milky white solution. After 1 h, the mixture was cooled in a refrigerator for 1 h and then filtered. The precipitate was washed with 1 N HCl to provide N-[(5-chloro-2-thienyl)sulfonyl]-3-ethylnorvaline as a white solid (18.5 g, 78%). Mass Spectrum (−ESI): 325 (M−H)⁻.

C. N-[(5-Chloro-2-thienyl)sulfonyl]-3-ethyl-L-norvaline (+)-(1S,2R)-Ephedrine hemihydrate (16.7 g, 95.6 mmol) was added to a suspension of N-[(5-chloro-2-thienyl) sulfonyl]-3-ethylnorvaline (31.2 g, 95.6 mmol) in 185 mL of EtOH. The mixture was heated slightly to dissolve solids and a precipitate formed. After cooling at 5° C. for 18 h the resulting suspension was filtered and the precipitate was washed with cold EtOH and EtOAc to give 27% yield of the diastereomeric salt. The salt was recrystallized from boiling EtOAc (420 mL), then filtered off. The resulting white solid was then dissolved in 300 mL of EtOAc and 300 mL of 1N HCl. The layers were separated and the organic extract was washed with 1N HCl (2×200 mL), dried ($Na_2SO_4$), and concentrated to give N-[(5-chloro-2-thienyl)sulfonyl]-3-ethyl-L-norvaline as a white solid (5.6 g, 18%). Chiral HPLC [chiralpak AD (25×0.46 cm), 8:2 hexane (0.1% TFA): isopropanol, L-isomer elutes at 9.6 min and D-isomer elutes at 13.1 min] indicated 96% chiral purity. $[\alpha]_D^{25}$=+44.5° (c=1% SOLUTION, MeOH). Mass Spectrum (−ESI): 325 (M−H)⁻ Anal. Calc'd for $C_{11}H_{16}ClNO_4S_2$: C, 40.55; H, 4.95; N, 4.30. Found: C, 40.30; H, 4.78; N, 4.16.

D. 5-Chloro-N-[(S)-2-ethyl-1-(hydroxymethyl)butyl]-2-thiophenesulfonamide

To N-[(5-Chloro-2-thienyl)sulfonyl]-3-ethyl-L-norvaline (5.6 g, 17.2 mmol) in THF (150 mL) at 0° C. was added a solution of 1 M borane tetrahydrofuran complex in THF (69 mL, 69 mmol) dropwise via addition funnel. After 15 min, the reaction mixture was warmed to 25° C. and stirred for 18 h. It was then quenched with 90 mL of 10% AcOH in MeOH slowly. Volatiles were removed in vacuo. The residue was then dissolved in EtOAc (300 mL) and washed with saturated aqueous $NaHCO_3$ (3×200 mL), dried ($Na_2SO_4$), and concentrated to a white precipitate (5.1 g, 96% yield, 96% chiral purity). The precipitate was recrystallized with heptane/EtOAc, 4:1, to give optically pure 5-chloro-N-[(S)-2-ethyl-1-(hydroxymethyl)butyl]-2-thiophenesulfonamide as white needles (4.4 g, 81% yield). $[\alpha]_D^{25}$=+4.5° (c=1% SOLUTION, DMSO). Mass Spectrum (−ESI): 310 (M−H)⁻. Anal. Calc'd for $C_{11}H_{18}ClNO_3S_2$: C, 42.37; H, 5.82; N, 4.49. Found: C, 42.37; H, 5.79; N, 4.38.

E. 5-Chloro-N-[(S)-2-ethyl-1-formylbutyl]thiophene-2-sulfonamide

Pyridinium dichromate (2.4 g, 6.4 mmol) was added to a solution of 5-chloro-N-[(S)-2-ethyl-1-(hydroxymethyl) butyl]-2-thiophenesulfonamide (0.5 g, 1.6 mmol) in $CH_2Cl_2$ (20 mL). After 18 h, the reaction mixture was filtered through a plug of Celite. The filtrate was concentrated and the resulting residue was purified by silica gel column chromatography (eluant: 1:4 EtOAc-hexane) to give 5-chloro-N-[(S)-2-ethyl-1-formylbutyl]thiophene-2-sulfonamide as a white solid (303 mg, 61%). $[\alpha]_D^{25}$=+136.76°(c=1% SOLUTION, $CHCl_3$). Mass Spectrum (−ESI): 308 (M−H)⁻. Anal. Calc'd for $C_{11}H_{16}ClNO_3S_2$: C, 42.64; H, 5.21; N, 4.52. Found: C, 42.57; H, 5.24; N, 4.52.

Example 2

Method 2

5-Chloro-N-[(S)-2-ethyl-1-formylbutyl]thiophene-2-sulfonamide

A. (S)-3-Ethyl-2-{[(S)-1-phenylethyl] amino } pentanenitrile

To (S)-(−)-α-methylbenzylamine hydrochloride salt (1.2 g, 7.6 mmol) in 80 mL of 1:1 MeOH/$H_2O$ was added potassium cyanide (0.5 g, 7.6 mmol) and 2-methylbutyraldehyde (0.94 mL, 7.6 mmol). A precipitate formed after 30 min. After 20 h, the suspension was filtered and washed with $H_2O$ to give (S)-3-ethyl-2-{[(S)-1-phenylethyl]amino}pentanenitrile as a white powder (1.29 g, 74%). Mass Spectrum (+ESI): 310 (M+H)+. Anal. Calc'd for $C_{15}H_{22}N_2$: C, 78.21; H, 9.63; N, 12.16. Found: C, 77.90; H, 9.75; N, 12.32.

B. 3-Ethyl-$N^2$-[(S)-1-phenylethyl]-L-norvalinamide

To 25 mL of sulfuric acid at 0° C. was added (S)-3-ethyl-2-{[(S)-1-phenylethyl]amino}pentanenitrile (2.7 g, 11.6 mmol) portionwise. The mixture was warmed to 25° C. After 2 days, the reaction mixture was poured over about 100 g of crushed ice. Concentrated $NH_4OH$ was added to neutralize the acid. This mixture was extracted with EtOAc (3×100 mL), dried over $Na_2SO_4$, filtered and concentrated to give 3-ethyl-$N^2$-[(S)-1-phenylethyl]-L-norvalinamide (2.6 g, 90%), which was used in the next step without purification. Mass Spectrum (+ESI): 249 (M+H)⁺. Anal. Calc'd for $C_{15}H_{24}N_2O$: C, 72.54; H, 9.74; N, 11.28. Found: C, 72.24; H, 10.04; N, 11.01

C. 3-Ethyl-L-norvalinamide

A mixture of 3-ethyl-$N^2$-[(S)-1-phenylethyl]-L-norvalinamide (2.6 g, 10.5 mmol) and 5% Pd/C (800 mg) was shaken for 24 h in a Parr apparatus under 3 atm of $H_2$. The mixture was filtered through a plug of Celite and the solvent was removed in vacuo to give 3-ethyl-L-norvalinamide as a white solid (1.4 g, 93%), which was used in the next reaction without further purification. Mass Spectrum (+ESI): 145 (M+H)⁺.

D. N-[(5-Chloro-2-thienyl)sulfonyl]-3-ethyl-L-norvaline

3-Ethyl-L-norvalinamide (1.2 g, 4.8 mmol) was dissolved in conc. HCl (10 mL) and heated to 100° C. for 16 h. The reaction mixture was concentrated to a white solid consisting of the amino acid hydrochloride salt and one equivalent of NH$_4$Cl, which was used in the next reaction without purification.

Amino acid hydrochloride salt with 1 equivalent of NH$_4$Cl (0.28 g, 1.19 mmol) was dissolved in 6 mL of H$_2$O and then NaOH (0.24 g, 6.00 mmol) was added. The solution was cooled to 0° C. and then 5-chlorothiophene-2-sulfonyl chloride (0.29 g, 1.32 mmol) in 6 mL of THF was added dropwise. The mixture was warmed to 25° C. After 19 h, THF was removed in vacuo. The remaining solution was diluted with 10 mL of H$_2$O and washed with EtOAc (2×10 mL). The solution was acidified with 1N HCl and a precipitate formed. This was filtered to give N-[(5-chloro-2-thienyl)sulfonyl]-3-ethyl-L-norvaline as a white solid (0.17 g, 44%). Chiral HPLC indicates that only the S enantiomer is present.

5-Chloro-N-[(S)-2-ethyl-1-(hydroxymethyl)butyl]-2-thiophenesulfonamide and 5-Chloro-N-[(S)-2-ethyl-1-formylbutyl]thiophene-2-sulfonamide were then prepared from N-[(5-Chloro-2-thienyl)sulfonyl]-3-ethyl-L-norvaline according to method 1 of Example 1.

Example 3

5-Chloro-N-[(S)-2-ethyl-1-(hydroxymethyl)butyl]-2-thiophenesulfonamide

Into a 3L 3-necked flask equipped with a nitrogen inlet tube, a mechanical stirrer, and an addition funnel with a stopper was placed lithium borohydride (145 mL of a 2 M solution in THF, 0.29 mol). The solution was placed under nitrogen and cooled to 0° C. Chlorotrimethylsilane (73.8 mL, 0.58 mol) was added dropwise over a period of 30 min. The ice bath was removed and the resulting slurry was stirred at room temperature for 30 min. The reaction mixture was cooled to 0° C. and the 2-(S)-amino-3-ethyl-pentanoic acid (21.1 g, 0.145 mol), which was prepared according to Scheme 13, was added in portions as a solid over a period of 15 min. The reaction mixture was allowed to warm slowly to room temperature as the ice bath melted. After 3 days at room temperature, the reaction mixture was cooled to 0° C., and methanol (217 mL) was carefully added over a period of 80 min. The solution was stirred at room temperature for an additional 40 min, then concentrated under reduced pressure in a water bath at 60° C. The resulting slurry was made basic with 20% sodium hydroxide (37.5 mL). Water (37.5 mL) was added, and the entire aqueous layer was extracted with methylene chloride (300 mL), and dried (Na$_2$SO$_4$). Concentration under reduced pressure gave 2(S)-amino-3-ethylpentanol as an oil (17.3 g, 91%), which was used immediately or stored in the freezer overnight: Opt. Rot. $[\alpha]_D^{25}$=−3.7° (1% solution, DMSO); $^1$H NMR (DMSO-d$^6$, 500 MHz): δ 4.38 (broad s, 1H), 3.35 (dd overlapping with a broad s at δ 3.32, J=4.5, 10.3 Hz, 3H), 3.14 (dd, J=7.9, 10.2 Hz, 1H), 2.63 (m, 1H), 1.45-1.05 (m, 5H), 0.82 and 0.81(two overlapping triplets, J=7.4 Hz, 6H); MS(+ESI): [M+H]$^+$, 132 (60%).

A mixture of 2(S)-amino-3-ethylpentanol (34.1 g, 0.26 mol) and methylene chloride (700 mL) was placed under Argon, and cooled to 0° C. Triethylamine (36.2 mL, 0.26 mol) was added, followed by the dropwise addition of 5-chlorothiophene-2-sulfonyl chloride (56.4 g, 0.26 mol) in methylene chloride (400 mL). The reaction mixture was allowed to warm slowly to room temperature as the ice bath melted. After 3 days at room temperature, the reaction mixture was divided into two-0.6 L portions. Each portion was diluted with ethyl acetate (1L), and washed three times with saturated potassium phosphate monohydrate (200 mL), once with brine (200 mL), and dried (Na$_2$SO$_4$). Concentration under reduced pressure gave a white solid (74.5 g, 92%). The product (87.98 g) from several runs were combined and recrystallized from hot heptane:ethyl acetate (4:1, 775 mL) to give the title compound as crystals (74.9 g, 85%): mp 115–117.6° C.; Opt. Rot. $[\alpha]_D^{25}$=+10.81° (1% solution, MeOH); $^1$H NMR (DMSO-d$^6$, 500 MHz): δ 7.71 (d, J=8.1 Hz, 1H), 7.44 (d, J=4.1 Hz, 1H), 7.22 (d, J=4.1 Hz, 1H), 4.56 (t, J=5.2 Hz, OH), 3.31–3.15 (m, 3H), 1.40-1.15 (m, 4H), 1.07 (m, 1H), 0.79 and 0.76 (two overlapping triplets, J=7.3 Hz, 6H); $^{13}$C NMR (DMSO-d$^6$, 100 MHz): δ 141.75, 133.73, 130.95, 127.60, 60.41, 56.89, 41.57, 21.31, 20.80, 11.79, 11.51; MS(−ESI): [M−H]$^{−1}$, 1 chlorine isotope pattern, 310(100%), 312 (30%); Anal. Calc. for C$_{11}$H$_{18}$ClNO$_3$S$_2$: C, 42.37, H, 5.82, N, 4.49. Found: C, 42.34, H, 5.65, N, 4.43. Chiral HPLC (Chiralpak AD, 25×0.46 cm, eluant 8:2 hexane/isopropanol containing 0.1% TFA, flow rate 0.5 mL/min, UV detection at 254 nm, retention times for the S and R isomers are 10.95 min and 11.95 min, respectively) revealed an S/R ratio of 100.0:0.0.

Example 4

5-Chloro-N-[(S)-2-ethyl-1-(1-hydroxyethyl)butyl]thiophene-2-sulfonamide

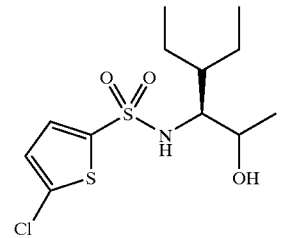

A solution of methylmagnesium bromide (1.4 M, 7.0 mL, 9.7 mmol) in toluene/THF (75:25) was added to a 0° C. solution of 5-chloro-N-[(S)-2-ethyl-1-formylbutyl]thiophene-2-sulfonamide (Example 1 or 2, 1.0 g, 3.2 mmol) in THF (30 mL). The mixture was warmed to 25° C. and after 2 h was quenched carefully with saturated aqueous ammonium chloride (25 mL). The mixture was extracted with EtOAc (3×25 mL). The organic extract was dried over Na$_2$SO$_4$, filtered and concentrated to give a colorless oil. The product was purified by column chromatography (Biotage), eluant: 1:4 EtOAc-hexane, to afford 5-chloro-N-[(S)-2-ethyl-1-(1-hydroxyethyl)butyl]thiophene-2-sulfonamide as a white solid (876 mg, 83%). The product is a diastereomeric mixture with a ratio of 3:7. mp 95–98° C. Anal. Calc'd for C$_{12}$H$_{20}$ClNO$_3$S$_2$: C, 44.23; H, 6.19; N, 4.30. Found: C, 44.25; H, 6.35; N, 4.29. Mass Spectrum (−ESI): 324 (M−H)$^−$.

Example 5

Assay Conditions

A. Semi-Preparative RP-HPLC Conditions:

Gilson Semi-Preparative HPLC system with Unipoint Software.

Column: Phenomenex C18 Luna 21.6 mm×60 mm, 5μ

Solvent A: Water (0.02% TFA buffer)

Solvent B: Acetonitrile (0.02% TFA buffer)
Solvent Gradient: Time 0:10% B; 2.5 min: 10% B; 14 min: 90% B.
Flow Rate: 22.5 mL/min
The product peak was collected based on UV absorption and concentrated.
B. Analytical LCMS Conditions:
Hewlett Packard 1100 MSD with ChemStation Software
Column: YMC ODS-AM 2.0 mm×50 mm 5μ column at 23° C.;
3 μL injection;
Solvent A: Water (0.02% TFA buffer)
Solvent B: Acetonitrile (0.02% TFA buffer)
Gradient: Time 0: 95% A; 0.3 min: 95% A; 4.7 min: 10% A; 4.9 min: 95% A.
Flow rate 1.5 mL/min;
Detection: 254 nm DAD;
API-ES Scanning Mode Positive 150–700; Fragmentor 70 mV.
C. Analytical LCMS Conditions:
ZMD (Waters) or Platform (Micromass) or LCZ (Micromass)
Column: Zorbax SB-C8
Solvent: Acetonitrile+$H_2O$ containing 0.1% TFA or 0.1% FA
Gradient: Gradient: 2.5 min 15% Acetonitrile—95% Acetonitrile
Flow rate 3 ml\min
Detection: ELSD detection (SEDEX 55)
UV 253 detection (Schimadzu)

Example 6

Repressor Release Assay (RRA)

The compounds generated as described in Examples 1 through 4 were tested in the RRA in accordance with published techniques [Shuey, D. J., Sheiffele, P., Jones, D., Cockett, M. I., and Quinet, E. M. (1999), "Repressor release: a useful tool for monitoring amyloid precursor protein (APP) proteolysis in mammalian cells", Society for Neuroscience Abstracts, Vol. 25, 29th Annual Meeting of Society for Neuroscience, Miami Beach, Fla., Oct. 23–28, 1999]. Briefly, this assay is performed as follows.

A. Cell Culture

CHO-K1 cells are cultured in whole DMEM media (DMEM—High Glucose with 10% fetal bovine serum, 1% Non-essential Amino Acids, and 1% Penicillin-Streptomycin) at 37° C. with 5% $CO_2$. Two million cells are plated into 10-cm dishes 24 hrs prior to transfection.

Transient transfections are completed as recommended by Gibco BRL using their Lipofectamine Plus system. First, 6 μg of pRSVO-luc and 6 μg of APP-lacI construct DNA are added to 460 μL Opti-Mem transfection media and incubated with 30 μL Plus reagent for 15 minutes. Then, a lipid mixture of 40 μL Lipofectamine reagent and 460 μL Opti-Mem transfection media is incubated with the DNA-Plus reagent mixture for 15 minutes. During the DNA-lipid incubation, the CHO-K1 cells are washed once and covered in 5.0 mL DMEM media without Penicillin-Streptomycin. The DNA-lipid preparation is then layered onto these cells and incubated at 37° C. overnight.

One and one half million transfected cells per well (100 μL total volume) are plated into sterile, opaque Packard 96-well Cultur-Plates in clear DMEM whole media (DMEM—without phenol red) and incubated at 37° C. with 5% $CO_2$ for 3–5 hours.

B. Compound Dilution

Compounds are diluted using two different protocols; one protocol is used for compounds supplied neat (weighed powder in vial) and the other protocol is used for compounds supplied in solution (20 mM in DMSO in 96-well plates). For both protocols, 25 mM Hepes and 25 mM Hepes/1% DMSO are prepared fresh to be used as diluent. The Hepes/DMSO is used as the diluent control on all experimental plates.

The following table depicts the steps for compound dilution (please note that the last step is the addition of compound to cells/media in tissue culture plate):

|  | Concentration | Dilution |
| --- | --- | --- |
| Stock Solution | 10 mg/mL | x mg compound (vial) diluted with 100% DMSO |
| Dilution 1 | 1 mg/mL | 20 μL stock solution 180 μL 25 mM Hepes |
| Dilution 2 | 200 μg/mL | 60 μL Dilution 1 240 μl 25 mM Hepes |
| Dilution 3 (in Cell Plate) | 20 μg/mL | 11.3 μL Dilution 2 (in 100 μL cells/well) |

Because some compounds arrive in 96-well format at 20 mM, the following represents the protocol for their dilution (note that an average molecular weight of these compounds was used to calculate these dilutions and as above, the last step is the addition of compound to cells/media in tissue culture plate):

|  | Concentration | Dilution |
| --- | --- | --- |
| Stock Solution (original conc.) | — | 20 mM Solution |
| Dilution 1 | ~200 μg/mL | 6 μL stock solution 194 μL 25 mM Hepes |
| Dilution 2 (in Cell Plate) | ~20 μg/mL | 11.3 μL Dilution 2 (in 100 μL cells/well) |

Once compounds are diluted, they are applied in duplicate on cells in tissue culture plates (prepared above). Cells are incubated with compound at 37° C with 5% $CO_2$ for an additional 36–48 hours.

C. Assay Measurement

Luciferase assays (LucLite reagent, Packard) are performed and are read on a Packard TopCount instrument. Media is removed from each 96-well plate and replaced with 100 μL PBS per well (with $Mg^{2+}$ and $Ca^{2+}$). An equal volume (100 μL) of the LucLite lysis/substrate buffer is added to each well and the plates are sealed and mixed in the dark on a rotary shaker for 15–30 minutes at room temperature. Luciferase readings are then taken on the TopCount instrument. Measurements are expressed as relative light units (RLU) and are calculated and analyzed in MS Excel as follows.

D. Analysis of data

The results of the assay with respect to the compounds exemplified herein are provided in the following table. A compound is considered active in RRA if it leads to at least a 1.5 fold increase in luciferase activity at 20 μM and is non-toxic, as determined by loss of signal (<0.75 fold increase). Fold increase is the amount of luciferase activity (measured in relative light units) over diluent control. SEM represents the standard error of the mean for fold increase (not shown). All compounds tested were found to be non-toxic.

TABLE

| Ex # | Conc (μg/mL) | APPI Fold Increase | Name |
|---|---|---|---|
| 1–3 | 20 | 4.9 | 5-chloro-N-[(S)-2-ethyl-1-formylbutyl]thiophene-2-sulfonamide |
| 4 | 20 | 7.2 9.7 | 5-chloro-N-[(S)-2-ethyl-1-(1-hydroxyethyl)butyl]thiophene-2-sulfonamide |

All publications cited in this specification are incorporated herein by reference. While the invention has been described with reference to a particularly preferred embodiment, it will be appreciated that modifications can be made without departing from the spirit of the invention. Such modifications are intended to fall within the scope of the appended claims.

What is claimed is:

1. A method for producing a chirally pure α-amino acid or a salt thereof comprising the steps of:
    (a) reacting an aldehyde and a cyanide salt with a chiral α-methylbenzylamine or a salt thereof and filtering to provide product (a);
    (b) reacting a strong inorganic acid and product (a);
    (c) neutralizing the acid of the reaction of (b);
    (d) extracting product (b) from the neutralized acid;
    (e) hydrogenating product (b) in the presence of a catalyst to provide product (c); and
    (f) hydrolyzing product (c) in a strong aqueous acid to provide a salt of a chirally pure α-amino acid.

2. The method of claim 1 further comprising the step of neutralizing the salt of chirally pure α-amino acid to provide the chirally pure α-amino acid.

3. The method according to claim 1, wherein the reacting step (a) is permitted to continue for 12 to 24 hours.

4. The method according to claim 1, wherein the reacting step (a) results in a suspension containing precipitate and further comprises the steps of filtering the suspension and washing the filtrate with water to provide a powder.

5. The method according to claim 1, wherein the cyanide salt is selected from among sodium cyanide and potassium cyanide.

6. The method according to claim 1, wherein the strong inorganic acid is sulfuric acid.

7. The method according to claim 6, wherein the sulfuric acid is at 0° C. when product (a) is added.

8. The method according to claim 1, wherein the strong inorganic base used in neutralizing step (c) is ammonium hydroxide.

9. The method according to claim 1, wherein the extracting step utilizes ethyl acetate as an extractant, and wherein the step further comprises the steps of drying, filtering, and concentrating to provide product (b).

10. The method according to claim 1, wherein in the hydrogenating step (e), the catalyst is palladium.

11. The method according to claim 1, wherein in the hydrogenating step (e), the mixture is pressurized to 3 atm.

12. The method according to claim 1, wherein the hydrolyzing step (f) is performed at a temperature of 100° C.

13. The method according to claim 1, wherein the hydrogenating step (e) further comprises the steps of filtering the mixture and removing solvent.

14. The method according to claim 1, wherein the hydrolyzing step (f) is performed over a period of 16 hours.

15. The method according to claim 1, wherein the hydrolyzing step (f) further comprises the step of concentrating the resulting reaction mixture to provide a product consisting of the amino acid hydrochloride salt and one equivalent of ammonium chloride.

16. The method according to claim 14, further comprising the steps of dissolving the product consisting of the amino acid hydrochloride salt and one equivalent of ammonium chloride in water and adding sodium hydroxide to form a solution.

17. The method according to claim 1, wherein the chiral α-amino acid is of the formula $(R)_2CH(CH_2)_nCH(CO_2H)(NH_2)$, where n is 0 to about 10 and R is selected from the group consisting of lower alkyl, substituted lower alkyl, lower alkenyl, substituted lower alkenyl, lower alkynyl, substituted lower alkynyl, cycloalkyl, substituted cycloalkyl, phenyl, substituted phenyl, benzyl, substituted benzyl, $CH_2$cycloalkyl, $CH_2$-3-indole, CH(loweralkyl)-2-furan, CH(loweralkyl)-4-methoxyphenyl, CH(loweralkyl)phenyl, and CH(OH)-4-$SCH_3$-phenyl.

18. A method for preparing a chiral 2-aminoalcohol, said method comprising the steps of:
    preparing a chiral α-amino acid according to claim 1;
    reducing the α-amino acid to the 2-aminoalcohol; and
    recrystallizing the 2-aminoalcohol to afford the chirally pure 2-aminoalcohol.

19. A method for resolving an N-sulfonyl α-amino acid having a β-branched alkyl substituent for use in preparing a chirally pure N-sulfonyl α-amino acid, comprising the steps of:
    (a) forming a mixture of chirally pure ephedrine hemihydrate and an N-sulfonyl α-amino acid in ethanol at a molar ratio of 1:1, wherein the N-sulfonyl α-amino acid is selected from the group consisting of N-sulfonyl β-ethylnorvaline, N-sulfonylvaline, and N-sulfonyl β-n-propylnorleucine;
    (b) heating the mixture of (a) to about 80° C. to dissolve the solids;
    (c) cooling the mixture to allow formation of a precipitate;
    (d) filtering the precipitate to give diastereomeric salt;
    (e) recrystallizing the diastereomeric salt;
    (f) dissolving the recrystallized salt in an organic solvent and strong aqueous acid and separating the layers to obtain an organic extract;
    (g) washing the organic extract; and
    (h) drying, concentrating and optionally recrystallizing the organic extract to provide chirally pure N-sulfonyl α-amino acid.

20. The method according to claim 19, wherein the N-sulfonyl ethylnorvaline is N-[(5-chloro-2-thienyl)sulfonyl]-3-ethylnorvaline; and wherein
    in step (d), the precipitate is washed with ethanol and ethyl acetate to give diastereomeric salt.

21. The method according to claim 19, wherein the cooling step is performed at 5° C. for 18 hours.

22. The method according to claim 19, wherein the cooling is permitted to occur at room temperature.

23. The method according to claim 19, further comprising the step of, following the cooling step, filtering the suspension formed.

24. The method according to claim 19, wherein the recrystallizing step is performed in boiling ethyl acetate.

25. The method according to claim 19, further comprising the step of filtering off the recrystallized salt.

26. The method according to claim 19, wherein the organic extract is washed with HCl.

27. The method according to claim 19, wherein the organic extract is dried with $Na_2SO_4$.

28. A method for preparing a chiral N-sulfonyl 2-aminoalcohol comprising the steps of:
 preparing a chiral N-sulfonyl α-amino acid according to claim 19;
 reducing the N-sulfonyl α-amino acid to the N-sulfonyl 2-aminoalcohol; and
 recrystallizing the N-sulfonyl 2-aminoalcohol to afford the chirally pure N-sulfonyl 2-aminoalcohol.

29. The method according to claim 28, wherein the N-sulfonyl α-aminoalcohol is of Formula (I), or pharmaceutically acceptable salt thereof, wherein Formula (I) has the structure:

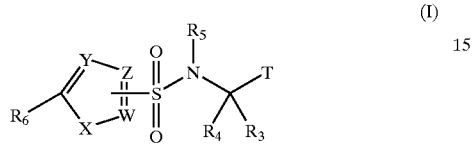

(I)

wherein:
 $R_1$ and $R_2$ are hydrogen;
 $R_3$ is selected from the group consisting of hydrogen, alkyl, and substituted alkyl;
 $R_4$ is selected from the group consisting of hydrogen, alkyl, substituted alkyl, alkylcycloalkyl, substituted alkylcycloalkyl, phenyl(substituted)alkyl, alkylOH, substituted alkylOH, alkylOBn, substituted alkylOBn, alkylpyridyl, substituted alkylpyridyl, alkylfuranyl, substituted alkylfuranyl, CH(OH)phenyl, CH(OH)substituted phenyl, alkenyl, substituted alkenyl, cycloalkyl, substituted cycloalkyl, N-substituted-piperidinyl, piperidinyl, substituted piperidinyl, tetrahydrothiopyran, substituted tetrahydrothiopyran, 2-indane, substituted 2-indane, phenyl, substituted phenyl, alkylNHR$_7$, and substituted alkylNHR$_7$;
 with the proviso that $R_3$ and $R_4$ are not both hydrogen;
 $R_7$ is alkyl, substituted alkyl, cycloalkyl, substituted cycloalkyl, benzyl, substituted benzyl, alkylOH, substituted alkylOH, alkylSR$_8$, or substituted alkylSR$_8$;
 $R_8$ is alkyl, substituted alkyl, benzyl, or substituted benzyl;
 or $R_3$ and $R_4$ may be joined to form a ring;
 $R_5$ is selected from the group consisting of hydrogen, lower alkyl, substituted lower alkyl, alkenyl, substituted alkenyl, alkynyl, substituted alkynyl, CH$_2$cycloalkyl, substituted CH$_2$cycloalkyl, benzyl, substituted benzyl, and CH$_2$CH$_2$QR$_9$;
 Q is O, NH or S;
 $R_9$ is lower alkyl, substituted lower alkyl, phenyl, or substituted phenyl;
 $R_6$ is selected from the group consisting of hydrogen, halogen and CF$_3$;
 T is

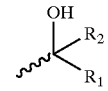

W, Y and Z are independently selected from the group consisting of C, CR$_{10}$ and N;
 $R_{10}$ is selected from the group consisting of hydrogen and halogen, with the proviso that at least one of W, Y and Z must be C;
 X is selected from the group consisting of O, S, SO$_2$, and NR$_{11}$;
 $R_{11}$ is selected from the group consisting of hydrogen, lower alkyl, substituted lower alkyl, benzyl, substituted benzyl, phenyl, and substituted phenyl;
 provided that when the compound contains one or more chiral centers, at least the β-amino alcohol chiral center must be of S-stereochemistry.

30. The method according to claim 29, wherein $R_6$ is halogen.

31. The method according to claim 29, wherein $R_6$ is chlorine or bromine.

32. The method according to claim 29, wherein T is C(OH)R$_1$R$_2$ and $R_1$ and $R_2$ are each hydrogen.

33. The method according to claim 29, wherein W and Z are both C.

34. The method according to claim 29, wherein $R_4$ is lower alkyl with S-stereochemistry at the β-amino alcohol chiral center.

35. The method according to claim 29, wherein X is S, W is C, Z is CR$_{10}$, $R_6$ is halogen, $R_4$ is lower alkyl with S-stereochemistry at the β-amino alcohol chiral center, $R_3$ is hydrogen, $R_5$ is hydrogen, and $R_1$ and $R_2$ are each hydrogen.

36. The method according to claim 29, wherein $R_3CR_4$ is cyclohexyl.

37. The method according to claim 29, wherein $R_3CR_4$ is piperidine or N-substituted piperidine.

38. The method according to claim 29, wherein X is S, and W, Y and Z are independently C or CR$_{10}$.

* * * * *

UNITED STATES PATENT AND TRADEMARK OFFICE
CERTIFICATE OF CORRECTION

PATENT NO.    : 6,657,070 B2
DATED         : December 2, 2003
INVENTOR(S)   : Resnick et al.

It is certified that error appears in the above-identified patent and that said Letters Patent is hereby corrected as shown below:

Column 1,
Line 31, replace "a-amino acids." with -- α-amino acids. --.

Column 4,
Line 36, delete "and the."

Column 7,
Lines 23 and 25, replace "cc-amino acids" with -- α-amino acids --.
Line 31, replace "a-amino acids." with -- α-amino acids. --.
Lines 36 and 37, replace "a-amino acids" with -- α-amino acids --.
Line 43, replace "α-amyloid" with -- β-amyloid --.

Column 9,
Line 44, replace "Forula (I)" with -- Formula (I) --.

Column 10,
Line 13, replace "P-branches" with -- α-amino acid --.

Column 11,
Line 2, replace αamino acid" with -- α-amino acid --.

Column 12,
Line 43, replace "a-amino acid" with -- α-amino acid --.

Column 24,
Line 18, replace "$[M-H]^{-1}$, 1" with -- $[M-H]^{-}$, 1 --.

Column 25,
Line 25, delete 1st occurrence of "Gradient:"

UNITED STATES PATENT AND TRADEMARK OFFICE
CERTIFICATE OF CORRECTION

PATENT NO. : 6,657,070 B2
DATED : December 2, 2003
INVENTOR(S) : Resnick et al.

It is certified that error appears in the above-identified patent and that said Letters Patent is hereby corrected as shown below:

Column 26,
Line 48, replace "(with $Mg^{2+ and\ Ca2+)}$." with -- (with $Mg^{2+}$ and $Ca^{2+}$). --.
Line 62, replace "( 0.75" with -- ($\leq$ 0.75 --.

Signed and Sealed this

First Day of June, 2004

JON W. DUDAS
*Acting Director of the United States Patent and Trademark Office*